United States Patent [19]
Tateno

[11] Patent Number: 6,162,763
[45] Date of Patent: Dec. 19, 2000

[54] HERBICIDAL COMPOSITION FOR THE CONTROL OF ANNUAL BLUEGRASS

[75] Inventor: Atsushi Tateno, Kanagawa, Japan

[73] Assignee: Japan Tobacco Inc., Kanagawa, Japan

[21] Appl. No.: 09/291,947

[22] Filed: Apr. 15, 1999

[30] Foreign Application Priority Data

Apr. 28, 1998 [JP] Japan ................................. 10-118673
Nov. 4, 1998 [JP] Japan ................................. 10-313098

[51] Int. Cl.$^7$ .................................................. A01N 63/00
[52] U.S. Cl. ........................................ 504/117; 435/254.1
[58] Field of Search .................... 504/117; 435/254.1

[56] References Cited

U.S. PATENT DOCUMENTS

| | | | |
|---|---|---|---|
| 4,755,207 | 7/1988 | Bannon | 71/79 |
| 4,902,333 | 2/1990 | Quimby, Jr. | 71/79 |
| 5,077,045 | 12/1991 | Roberts | 424/93 |
| 5,192,541 | 3/1993 | Savage et al. | 424/93 D |
| 5,271,932 | 12/1993 | Savage et al. | 424/93 D |
| 5,559,079 | 9/1996 | Imaizumi et al. | 504/117 |

FOREIGN PATENT DOCUMENTS

| | | |
|---|---|---|
| 5268946 | 10/1993 | Japan . |
| 6292461 | 10/1994 | Japan . |
| 6343459 | 12/1994 | Japan . |

OTHER PUBLICATIONS

S. Imaizumi et al., J. Weed Sci. Tech., 42(1), pp. 8–17 (1997).

S. Imaizumi et al., J. Weed Sci. Tech., 42(2), pp. 115–124 (1997).

S. Imaizumi et al., J. Weed Sci. Tech., 42(2), pp. 125–134 (1997).

S. Imaizumi et al., Journal Japanese Society of Turfgrass Science 26(2), pp. 149–156 (1998).

S. Imaizumi et al., Biological Control, 8, pp. 7–14 (1997).

T. Nishino et al., Ann. Phytopathol. Soc.Jpn., 61(6), pp. 555–561 (1997).

T. Nishino et al., Ann. Phytopathol. Soc.Jpn., 62(5), pp. 492–494 (1996).

T. Nishino et al., Ann. Phytopathol. Soc.Jpn., 64(1), pp. 1–6 (1998).

T. Nishino et al., J. Pesticide Sci., 22(4), pp. 326–330 (1997).

T. Nishino et al., J. Pesticide Sci., 23(2), pp. 141–144 (1998).

T. Nishino et al., J. Pesticide Sci., 23(2), pp. 151–154 (1998).

*Primary Examiner*—S. Mark Clardy
*Attorney, Agent, or Firm*—Birch, Stewart, Kolasch & Birch, LLP

[57] ABSTRACT

A herbicidal composition for the control of annual bluegrass, comprising, as active ingredients, a microorganism belonging to the genus Xanthomonas and having control ability against annual bluegrass and paraffin is disclosed. This composition exhibits excellent herbicidal effect against annual bluegrass, but does not cause any phytotoxicity in various turfgrasses.

13 Claims, No Drawings

HERBICIDAL COMPOSITION FOR THE CONTROL OF ANNUAL BLUEGRASS

BACKGROUND OF THE INVENTION

1. Field of the Invention

The present invention relates to a herbicidal composition for the control of annual bluegrass (*Poa annua*) comprising a microorganism belonging to the genus Xanthomonas.

2. Prior Art

Annual bluegrass which is grows abundantly on golf courses, city parks, athletic grounds and so forth is the most strong, harmful weed in the turf. This weed is widely distributed throughout the world. In particular, annual bluegrass mixed with the turf of golf courses, such as putting greens, tee grounds, fairways and roughs, propagates at all times in spite of frequent mowing, and scatters a large quantity of seeds into the turf all the year round. At present, there are a number of herbicides developed for the control of annual bluegrass.

However, abundant use of agricultural chemicals at golf courses has become a major social problem as overuse causes environmental pollution. Among currently used chemical herbicides, there is no foliar treatment agent which can selectively kill annual bluegrass mixed with American and European lawn grasses, such as bentgrass, bluegrass, ryegrass and fescues, without harming the desirable turfgrasses. Therefore, for the maintenance of bent green, manual weeding or even total renewal of turf is inevitably required, and the cost of which is tremendous.

Under such circumstances, the present inventor and others have developed and commercialized a herbicide (product name: Camperico Liquid Formulation) in Japan which comprises, as active ingredients, *Xanthomonas campestris* P-482 and P-484 strains and selectively controls annual bluegrass without polluting the environment.

In order for Camperico Liquid Formulation to work, the microorganisms contained therein must be contacted with fresh wounds of annual bluegrass immediately after mowing. Thus, frequently, there is disparity in effect depending on mowing conditions and uneven application. Even if a large-scale application has been conducted to avoid unevenness, most of the applied liquid formulation may drop off due to the wax layer on the surface of annual bluegrass and, thus, sufficient herbicidal effects may not be achieved. Although an attempt to use a sulfonylurea compound in combination with the Xanthomonas microorganism to improve the herbicidal effect has been made (Japanese Unexamined Patent Publication No. 7-187937), the chemical herbicide contained may cause phytotoxicity when applied to turf immediately after renewal or germination. Thus, this combination cannot be used at such times. Furthermore, in view of the possible environmental pollution which might be caused by the chemical herbicide contained, it is desirable to avoid this combined use.

As described above, Camperico Liquid Formulation developed by the present inventors still have various aspects to be improved, though it has an epoch-making effect as compared to conventional herbicides.

OBJECTS AND SUMMARY OF THE INVENTION

It is an object of the present invention to solve the problems if which Camperico Liquid Formulation and to provide a more effective herbicide.

Toward the solution of the problems, the present inventor has mixed a paraffin-type spreader with a Xanthomonas microorganism having control ability against annual bluegrass, and treated annual bluegrass with the mixture in a specific manner. As a result, the inventor has found that the microorganism's control ability against annual bluegrass was remarkably improved and that the mixture did not cause phytotoxicity in turfgrasses other than the annual bluegrass. Thus, the present invention has been achieved.

The present invention relates to a herbicidal composition for the control of annual bluegrass, comprising, as active ingredients, a microorganism belonging to the genus Xanthomonas and having control ability against annual bluegrass and paraffin.

This specification includes part or all of the contents as disclosed in the specification of Japanese Patent Application Nos. 118673/1998 and 313098/1998 which are priority documents of the present application.

DETAILED DESCRIPTION OF THE INVENTION

Herein below, the present invention will be described in more detail.

The herbicidal composition of the invention for the control of annual bluegrass is characterized by comprising, as active ingredients, a microorganism belonging to the genus Xanthomonas and having control ability against annual bluegrass and paraffin.

The microorganism to be used is not particularly limited as long as it belongs to the genus Xanthomonas and has control ability against annual bluegrass. Preferably, a microorganism belonging to *Xanthomonas campestris* is used; *Xanthomonas campestris* P-482 strain or P-484 strain is especially preferable. The P-482 strain and P-484 strain were deposited at the National Institute of Bioscience and Human-Technology, Agency of Industrial Science and Technology, Japan under Accession Nos. FERM BP-4431 and FERM BP-4430, respectively (date of deposit: Oct. 1, 1993).

No special methods are required for culturing the microorganism to be used in the invention. It may be cultured according to conventional methods. As a medium, either a synthetic medium or natural medium may be used as long as it appropriately contains assimilable carbon sources, nitrogen sources, inorganic substances and necessary growth promoting substances. For example, YNB (yeast and nutrient broth) medium, NA (nutrient agar) medium or the like may be used. During the cultivation, it is preferred that the temperature be maintained at 5–40° C., preferably 28–31° C. and that the pH be maintained at 5–9, preferably 6–7. When the microorganism has been grown for 2 to 4 days under such conditions, a sufficient amount of cells can be obtained. In the preparation of the composition of the present invention, use of cells per se is preferable. Cells may be recovered by centrifugation of the culture fluid of the microorganism.

As paraffin, a paraffin contained in a commercial paraffin-type spreader may be used. Specifically, n-paraffin, paraffin wax, liquid paraffin, or the like may be used. These paraffins may be used independently or in combination.

Preferably, the herbicidal composition of the invention further comprises an emulsifier in addition to the above-mentioned microorganism and paraffin. The emulsifier may be an emulsifier contained in a commercial paraffin-type spreader. Specifically, sucrose fatty acid esters, polyoxyethylene sorbitan esters, sorbitan esters or the like may be used. These emulsifiers may be used independently or in combination.

A method for preparing the herbicidal composition of the invention is not particularly limited. However, since a commercial paraffin-type spreader contains both paraffin and an emulsifier, it is preferable to mix an appropriate microorganism with a commercial paraffin-type spreader. Specific examples of the paraffin-type spreader include, but are not limited to, "Panguard A" from Ohara Palladium Co. (Registration No. under Agricultural Chemicals Regulation Law, Article 2 (hereinafter abbreviated to "Registration No."): 14338; paraffin content: 16%), "Yashima Steckel" from Yashima Chemical Ind. Co. (Registration No. 11984; paraffin content: 24%), "Abion-E" from Abion Corporation (Registration No. 12058; paraffin content: 24%), "Sankei-chick" from Sankei Chemical Co. (Registration No. 13049; paraffin content: 24%), "Kikunoh" from Sanwa Chemical Co. (Registration No. 15715; paraffin content: 24%), "Thruate 24" from Yashima Sangyo Co. (Registration No. 15851; paraffin content: 24%), "Petan V" from Agro-Kanesho Co. (Registration No. 14931; paraffin content: 24%) and "Agroguard" from Agro-Kanesho Co. (Registration No. 18428; paraffin content: 24%). Any of these paraffin-type spreaders is a white, emulsifiable liquid containing paraffin at a rate of 16, 24 or 42% which is conferred emulsification stability.

The formulation of the herbicidal composition of the invention is not particularly limited. However, it is preferable to use the herbicidal composition as a liquid formulation. In this case, a microorganism may be suspended in an aqueous solution of a spreader which has been prepared to give a specific concentration; or a spreader may be added to a suspension of a microorganism.

When the herbicidal composition is used as a liquid formulation, the microorganism concentration in the formulation is in the range from $10^1$ CFU/ml to $10^{11}$ CFU/ml, preferably from $10^5$ CFU/ml to $10^9$ CFU/ml. As a result of the mixing of paraffin, a practical herbicidal effect can be expected at a concentration about 10 times lower than that in the herbicidal composition disclosed in Japanese Unexamined Patent Publication No. 7-187937. Also, because of the improvement in drug adhesion as a result of the mixing of paraffin, the amount of application necessary to achieve a practical herbicidal effect has been reduced to approximately ½, as compared to the above-mentioned herbicidal composition.

Preferably, the paraffin concentration in the liquid formulation is in the range from 0.001 to 40% by weight, more preferably from 0.01 to 20% by weight, and most preferably from 0.24 to 10% by weight.

When the herbicidal composition of the invention is actually applied to a field, it is preferred that the microorganism be applied at a rate of $10^{10}$–$10^{14}$ CFU per 10 ares and that the paraffin be applied at a rate of 10 g to 20 kg per 10 ares of the field. Although the herbicidal composition of the invention controls annual bluegrass, it does not exhibit any pathogenicity against major turfgrasses grown on golf courses, such as bentgrass, Kentucky bluegrass, perennial ryegrass, Italian ryegrass, Bermuda grass, tall oatgrass, timothy grass, tall fescue, red fescue, chewing fescue and hard fescue, as well as other gramineous crops.

EXAMPLE 1

Annual bluegrass seeds (0.5 g; approximately 1500 grains) were sown in planters (20 cm broad×10 cm long×8 cm deep) filled with sand and fertilizers, and grown in a greenhouse until seedlings have 4 to 5 leaves. Then, they were cut to a height of approximately 2.5 cm with an electric lawn mower. To these seedlings, the following five test liquids were applied with a sprayer at a rate of 2 ml/planter (100 ml/m²).

Test Liquid 1: a liquid formulation containing $1 \times 10^7$ CFU/ml of P-482 strain and 1.0% by volume of Thruate 24 (Yashima Sangyo Co.)

Test Liquid 2: distilled water

Test Liquid 3: a microorganism suspension containing $1 \times 10^7$ CFU/ml of P-482 strain Test Liquid 4: a liquid formulation containing $1 \times 10^7$ CFU/ml of P-482 strain and 0.05% by weight of imazasulfuron Test Liquid 5: a liquid formulation containing $1 \times 10^7$ CFU/ml of P-482 strain and 0.02% by volume of Neo-Esterin (Kumiai Chemical Industry Co.)

Thruate 24 is a paraffin-type spreader and Neo-Esterin a non-paraffin-type spreader. Test Liquid 4 is the liquid formulation disclosed in Japanese Unexamined Patent Publication No. 7-187937.

The plants thus treated were transferred into cultivation rooms in which day temperature/night temperature were adjusted at 25° C./20° C., 20° C./15° C. and 15° C./10° C., respectively. After two weeks, the number of remaining plants was counted to determine percent control. The test was repeated three times for each of the test liquids to thereby obtain the mean number of plants remaining. From this value, percent control was calculated using the following formula:

Percent control=[(No. of plants tested−No. of plants remaining)/ No. of plants tested]×100

The results are shown in Table 1.

TABLE 1

| Environmental Temp. (day/night) | Test Liquid 1 | Test Liquid 2 (control) | Test Liquid 3 (control) | Test Liquid 4 (control) | Test Liquid 5 (control) |
| --- | --- | --- | --- | --- | --- |
| 25° C./20° C. | 99 | 0 | 62 | 74 | 60 |
| 20° C./15° C. | 84 | 0 | 38 | 41 | 32 |
| 15° C./10° C. | 56 | 0 | 3 | 12 | 4 |

As shown in Table 1, when a paraffin-type spreader is mixed (Test Liquid 1), percent control is remarkably improved as compared to Test Liquid 3 in which the microorganism is used alone and Test Liquid 4 in which imazasulfuron is mixed. On the other hand, when a non-paraffin-type spreader is mixed (Test Liquid 5), such improvement in percent control is not observed.

EXAMPLE 2

To 200 ml of Camperico Liquid Formulation (Japan Tobacco Inc.) diluted to 1/1000 with distilled water, the six spreaders shown in Table 2 were added separately. Two hours after the addition, viable cell concentration was determined. Besides, the spreader-added Camperico Liquid Formulation was applied to annual bluegrass with a sprayer in the same manner as in Example 1. Two weeks after the application, the state of the treated plants was observed to compare the herbicidal effect with the effect produced when Camperico Liquid Formulation was used alone. The results are shown in Table 3.

TABLE 2

| Spreader | Usual Amount of Use (per 200 ml of dilution) | Amount of Addition (per 200 ml of dilution) |
|---|---|---|
| Abion-E | 0.4 ml–2.0 ml | 2.0 ml |
| Sankei-chick | 2.0 ml–2.4 ml | 2.4 ml |
| Thruate 24 | 0.5 ml–2.0 ml | 2.0 ml |
| Petan V | 0.2 ml–1.0 ml | 1.0 ml |
| Neo-Esterin | 0.001 ml–0.04 ml | 0.04 ml |
| Surfactant WK | 0.2 ml–1.0 ml | 1.0 ml |
| No addition | — | — |

TABLE 3

| Spreader | | Viable Cell Concentration | Herbicidal Effect |
|---|---|---|---|
| Avion-E | Paraffin-type | $1.9 \times 10^8$ CFU/ml | Herbicidal effect improved |
| Sankei-chick | Paraffin-type | $2.0 \times 10^8$ CFU/ml | Effect not confirmed |
| Thruate 24 | Paraffin-type | $2.0 \times 10^8$ CFU/ml | Herbicidal effect improved |
| Petan V | Paraffin-type | $2.1 \times 10^8$ CFU/ml | Herbicidal effect improved |
| Neo-Esterin | Non-paraffin-type | $6.7 \times 10^7$ CFU/ml | Herbicidal effect unchanged |
| Surfactant WK | Non-paraffin-type | Under detection limit | No effect was observed because of cell death |
| No addition | | $2.2 \times 10^8$ CFU/ml | — |

As shown in Table 3, herbicidal effect was improved when a paraffin-type spreader was mixed, but no such improvement was observed when a non-paraffin-type spreader was mixed. Besides, the addition of a paraffin-type spreader does not affect the viable cell count, while some non-paraffin type spreaders cause cell death.

EXAMPLE 3

Abion-E (Abion Corporation; paraffin-type spreader) was diluted with distilled water to give paraffin concentrations of 0.24%, 0.48%, 1%, 3%, 5% and 10%. To each of the resultant solutions, Camperico Liquid Formulation (Japan Tobacco Inc.) was added to make a 10000-fold dilution (viable cell concentration: approx. $2.0 \times 10^7$ CFU/ml). Thus, herbicidal compositions for the control of annual bluegrass were prepared. These compositions were applied to annual bluegrass with a sprayer in the same manner as in Example 1. As a control, Camperico Liquid Formulation was used alone.

The plants treated as described above were transferred into a cultivation room in which day temperature/night temperature were adjusted at 20° C./15° C. After two weeks, the number of remaining plants was counted to determine percent control. The test was repeated three times for each of the test liquids, and percent control was calculated in the same manner as in Example 1.

The results are shown in Table 4.

TABLE 4

| Paraffin Concentration | No. of Remaining Plants | | | Average No. of Remaining Plants | Percent Control |
|---|---|---|---|---|---|
| (%) | 1st Test | 2nd Test | 3rd Test | | |
| Camperico alone | 912 | 872 | 781 | 855 | 41.4 |
| 0.24 | 343 | 361 | 571 | 425 | 70.9 |
| 0.48 | 334 | 420 | 315 | 356 | 75.6 |
| 1.0 | 242 | 227 | 403 | 291 | 80.1 |
| 3.0 | 195 | 212 | 292 | 233 | 84.0 |
| 5.0 | 162 | 257 | 328 | 249 | 82.9 |
| 10.0 | 160 | 124 | 194 | 159 | 89.1 |
| No treatment | 1418 | 1427 | 1534 | 1460 | — |

As shown in Table 4, a remarkable improvement in herbicidal effect was confirmed in the paraffin concentration range from 0.24 to 10%, as compared to the effect produced by Camperico Liquid Formulation alone.

These herbicidal compositions containing paraffin at a concentration of 0.24 to 10% were applied to manillagrass and creeping bentgrass which are major turfgrasses. As a result, no phytotoxicity was recognized.

All publications, patents and patent applications cited herein are incorporated herein by reference in their entirety.

EFFECT OF THE INVENTION

Since the herbicidal composition of the present invention exhibits excellent herbicidal effect against annual bluegrass and does not cause any phytotoxicity in various turfgrasses, it is extremely useful as a herbicide to be applied to golf courses and sports fields.

What is claimed is:

1. A herbicidal composition for the control of annual bluegrass, comprising:

as active ingredients, a microorganism belonging to the genus Xanthomonas and having control ability against annual bluegrass; and paraffin.

2. The herbicidal composition for the control of annual bluegrass of claim 1, wherein the said microorganism belonging to the genus Xanthomonas and having control ability against annual bluegrass is a microorganism belonging to *Xanthomonas campestris*.

3. The herbicidal composition for the control of annual bluegrass of claim 1, wherein the said microorganism belonging to the genus Xanthomonas and having control ability against annual bluegrass is *Xanthomonas campestris* P-482 strain or *Xanthomonas campestris* P-484 strain.

4. The herbicidal composition for the control of annual bluegrass of any one of claims 1 to 3, wherein said composition further comprises an emulsifier.

5. The herbicidal composition of claim 1, wherein said paraffin is in-paraffin, paraffin wax, or liquid paraffin.

6. The herbicidal composition of claim 4, wherein said emulsifier is a sucrose fatty acid ester, a polyoxyethylene sorbitan ester or a sorbitan ester.

7. The herbicidal composition of claim 1, wherein said herbicidal composition is in a liquid formulation.

8. The herbicidal composition of claim 7, wherein the concentration of said microorganism in said liquid formulation is in the range from $10^1$ CFU/ml to $10^{11}$ CFU/ml.

9. The herbicidal composition of claim 7, wherein the concentration of said microorganism in said liquid formulation is in the range from $10^5$ CFU/ml to $10^9$ CFU/ml.

10. The herbicidal composition of claim 7, wherein the concentration of said paraffin in said liquid formulation is in the range of 0.001 to 40% by weight.

11. The herbicidal composition of claim 7, wherein the concentration of said paraffin in said liquid formulation is in the range from 0.01 to 20% by weight.

12. The herbicidal composition of claim 7, wherein the concentration of said paraffin in said liquid formulation is in the range from 0.24 to 10% by weight.

13. A method for the control of annual bluegrass comprising the steps of:

applying to annual bluegrass the herbicidal composition of claim 1.

* * * * *